United States Patent
Yan et al.

(10) Patent No.: US 9,526,884 B2
(45) Date of Patent: Dec. 27, 2016

(54) MECHANICALLY ROBUST FAST-DISSOLVING MICRONEEDLES FOR TRANSDERMAL DRUG AND VACCINE DELIVERY

(71) Applicant: CITY UNIVERSITY OF HONG KONG, Kowloon (HK)

(72) Inventors: Li Yan, Kowloon (HK); Xianfeng Chen, Sha Tin (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 693 days.

(21) Appl. No.: 13/679,301

(22) Filed: Nov. 16, 2012

(65) Prior Publication Data

US 2014/0142541 A1    May 22, 2014

(51) Int. Cl.
| | | |
|---|---|---|
| A61M 37/00 | (2006.01) | |
| A61K 9/51 | (2006.01) | |
| A61K 9/00 | (2006.01) | |
| A61K 47/38 | (2006.01) | |
| B82Y 5/00 | (2011.01) | |

(52) U.S. Cl.
CPC ........ *A61M 37/0015* (2013.01); *A61K 9/0021* (2013.01); *A61K 9/5115* (2013.01); *A61K 47/38* (2013.01); *B82Y 5/00* (2013.01); *A61M 2037/0046* (2013.01); *A61M 2037/0053* (2013.01)

(58) Field of Classification Search
CPC ................. A61M 37/0015; A61M 2037/0046; A61M 2037/0053; A61K 9/5115; A61K 47/38; A61K 9/0021; B82Y 5/00
See application file for complete search history.

(56) References Cited

U.S. PATENT DOCUMENTS

| | | |
|---|---|---|
| 6,261,554 B1 | 7/2001 | Valerio et al. |
| 6,620,617 B2 | 9/2003 | Mathiowitz et al. |
| 6,924,087 B2 | 8/2005 | Yeshurun et al. |
| 7,112,442 B2 | 9/2006 | Rice et al. |
| 8,162,901 B2 | 4/2012 | Gonnelli et al. |
| 2009/0182306 A1* | 7/2009 | Lee et al. ............ 604/506 |

(Continued)

FOREIGN PATENT DOCUMENTS

| | | |
|---|---|---|
| EP | 1195440 A1 | 4/2002 |
| WO | 2004/035105 A2 | 4/2004 |

(Continued)

OTHER PUBLICATIONS

Ladewig et al, Layered double hydroxide nanoparticles in gene and drug delivery, 2009, Expert Opin. Drug Deliv., 6(9), pp. 907-922.*

(Continued)

*Primary Examiner* — Trevor Love
(74) *Attorney, Agent, or Firm* — Heslin, Rothenberg, Farley & Mesiti, P.C.

(57) ABSTRACT

Disclosed are biocompatible, dissolving microneedle structures with enhanced mechanical strength. More particularly, the present disclosure relates to microneedles containing nanomaterials. Also disclosed are methods of producing such microneedle structures, as well as methods for using them to deliver drugs or biomolecules into the skin or epithelia, or the cytoplasm and/or nucleus of a skin or epithelia cell, of a subject.

14 Claims, 8 Drawing Sheets

(56) References Cited

U.S. PATENT DOCUMENTS

2011/0098651 A1* 4/2011 Falo et al. .................. 604/173

FOREIGN PATENT DOCUMENTS

| WO | 2010/071918 A1 | 7/2010 |
|---|---|---|
| WO | 2010082008 A1 | 7/2010 |
| WO | 2011/076537 A1 | 6/2011 |

OTHER PUBLICATIONS

Han, et al., "Gene Expression Using an Ultrathin Needle Enabling Accurate Displacement and Low Invasiveness." Elsevier, Biochemical and Biophysical Research Communications 332 (2005) pp. 633-639.
Yum, et al., "Mechanochemical Delivery and Dynamic Tracking of Fluorescent Quantum Dots in the Cytoplasm and Nucleus of Living Cells." Nano Letters, 2009, vol. 9, No. 5, pp. 2193-2198.
Zhang, et al., "Oriented Single-Crystal Diamond Cones and Their Arrays." Applied Physics Letter, 2003, vol. 82, No. 16, pp. 2622-2624.
Mehier-Humbert, et al., "Physical Methods for Gene Transfer: Improving the Kinetics of Gene Delivery Into Cells." Elsevier, Advanced Drug Delivery Reviews 57, 2005, pp. 733-753.
Yum, et al., "Nanoneedle: A Multifunctional Tool for Biological Studies in Living Cells," Nanoscale, first published as an Advance Article on the web Dec. 9, 2009.
Chen, et al., "A Cell Nanoinjector Based on Carbon Nanotubes," PNAS, 2007, vol. 104, No. 20, pp. 8218-8222.
Zhang, et al., "Structuring Nanodiamond Cone Arrays for Improved Field Emission." Applied Physics Letters, 2003, vol. 83, No. 16, pp. 3365-3367.
Kim, et al., "Interfacing Silicon Nanowires with Mammalian Cells." JACS, 2007, vol. 129, No. 23, pp. 7228-7229.
Shalek, et al., "Vertical Silicon Nanowires as a Universal Platform for Delivery Biomoleculres into Living Cells," PNAS, 2010, vol. 107, No. 5, pp. 1870-1875.
Foerg, et al., "On the Biomedical Promise of Cell Penetrating Peptides: Limits Versus Prospects." Journal of Pharmaceutical Sciences, 2008, vol. 97, No. 1, pp. 144-162.
Rubinsky, "Irreversible Electroporation in Medicine." Technology in Cancer Research and Treatment, 2007, vol. 6, No. 4, pp. 255-259.
Savulescu, "Harm, Ethics Committees and the Gene Therapy Death." Journal of Medical Ethics, 2001, vol. 27, pp. 148.150.
Chaudhri B.P. et al., Out-of-plane, high strength, polymer microneedles for transdermal drug delivery, IEEE (2011) 3680-3683.
Chu L.Y. et al., Fabrication of Dissolving Polymer Microneedles for Controlled Drug Encapsulation and Delivery: Bubble and Pedestal Microneedle Designs, Journal of Pharmaceutical Sciences, (Oct. 2010), vol. 99, No. 10, 4228-4238.
Kim C.S. et al., Efficient and facile delivery of gold nanoparticles in vivo using dissolvable microneedles for contrast-enhanced optical coherence tomography, Biomedical Optics Express (Aug. 2, 010), vol. 1, No. 1, 106-113.
Lee J.W. et al., Dissolving microneedles for transdermal drug delivery, Biomaterials 29 (2008) 2113-2124.
Martin C.J. et al., Low temperature fabrication of biodegradable sugar glass microneedles for transdermal drug delivery applications, J. Control. Release 158 (2012) 93-101.
Park J.H. et al., Biodegradable polymer microneedles: Fabrication, mechanics and transdermal drug delivery, J. Control. Release 104 (2005) 51-66.
Park J. et al., Analysis of Mechanical Failure of Polymer Microneedles by Axial Force, J Korean Phys Soc. (Apr. 2010); 56(4): 1223-1227.
Raphael A.P. et al., Targeted, needle-free vaccinations in skin using multi layered, densely packed dissolving microprojection arrays, Small 6 (2010) 1785-1793.
Sullivan S.P. et al., Minimally invasive protein delivery with rapidly dissolving polymer microneedles, Adv. Mater. 20 (2008) 933-938.
Sullivan S.P. et al., Dissolving polymer microneedle patches for influenza vaccination, Nat. Med. 16 (2010) 915-920.
Wang Q. et al., Recent Advances in the Synthesis and Application of Layered Double Hydroxide (LDH) Nanosheets, Chemical Reviews 112 (2012) 4124-4155.

\* cited by examiner

US 9,526,884 B2

MECHANICALLY ROBUST FAST-DISSOLVING MICRONEEDLES FOR TRANSDERMAL DRUG AND VACCINE DELIVERY

BACKGROUND OF THE INVENTION

Technical Field

The present disclosure generally relates to biocompatible, dissolving microneedle structures with enhanced mechanical strength. More particularly, the present invention relates to microneedles containing well dispersed nanomaterials.

Background Information

Microneedles are tiny projections of micrometer dimensions and have the capability of delivering drugs, vaccines and other biomolecules to skin. This transdermal delivery platform has many advantages over conventional subcutaneous and intramuscular injection by needle and syringe. First, there is no or minimal pain, cross-infection and needle stick injuries. Second, microneedles can be designed to target a specific layer of skin. Third, there is potential for self-administration. Last but not least, it can be used when there is a significant first-pass effect of the liver that can prematurely metabolize drugs. Microneedle arrays are usually made of silicon, metals and polymers. Among them, polymer microneedle arrays are increasingly attractive because they are expected to be less expensive to mass produce than silicon or metal arrays and safer during application. Drugs and biomolecules can be incorporated into the interior of microneedles themselves when using dissolving polymers. During application, the polymer structure rapidly dissolves in skin, thereby releasing the drug and biomolecules, so there is no sharp waste.

Despite their promising features, dissolvable polymers generally have relatively weak mechanical properties. The need for combination of biocompatibility, robust mechanical properties and rapid dissolution rate severely limits the choice of polymer. Polyvinylpyrrolidone (PVP) and carboxymethylcellulose sodium salt (CMC) are commonly reported for use in dissolving polymer microneedles. For example, PVP microneedles were fabricated by either in-situ polymerization of monomers under UV conditions (using a 100 W UV lamp) or heating at 80° C. for 24 hours. These harsh conditions may seriously limit the incorporation of drug and biomolecules that are temperature or UV sensitive. On the other hand, CMC microneedles can be fabricated at room temperature, but CMC has weak mechanical properties. For example, the elastic modulus of CMC is only around 1 GPa. It is expected that the bioresorbable polymer microneedle size needs to be relatively large to reliably pierce human skin. This would apparently limit the density of microneedles on an array. However, recent study shows that small (base diameter or width <40 μm) and densely packed microneedles (over 10,000 microneedles per cm$^2$) may lead to significantly enhanced vaccine efficacy when compared to large and sparsely packed ones. In addition, small microneedles can be easily dried during fabrication and dissolve rapidly in skin during application. Therefore, improving the mechanical properties of dissolving polymer microneedles could be beneficial in terms of drug efficacy and design flexibility as well as ease in fabrication and rapid dissolution in the skin.

Thus, a need exists for improved mechanical characteristics of dissolving microneedle arrays for transdermal delivery.

SUMMARY OF THE INVENTION

In a first aspect, a microneedle structure is disclosed comprising a plurality of microneedles, wherein each of the microneedles is comprised of at least one dissolvable polymer and a nanomaterial, wherein the nanomaterial is well-dispersed throughout each of the microneedles.

In a second aspect, a method is disclosed for producing a microneedle structure. The steps of this method include a) forming a composite solution comprising at least one dissolvable polymer and at least one nanomaterial, wherein the nanomaterial is well-dispersed throughout the composite solution; b) adding the composite solution to the surface of a microneedle structure mold; c) forcing the composite solution to the microneedle structure mold cavity; d) drying the composite solution to form a microneedle structure; and e) removing the microneedle structure from the microneedle structure mold.

In a third aspect, a method is disclosed for producing a microneedle structure of increased mechanical strength. The steps of this method include a) forming a composite solution comprising at least one dissolvable polymer and at least one nanomaterial, wherein the nanomaterial is well-dispersed throughout the composite solution; b) adding the composite solution to the surface of a microneedle structure mold; c) forcing the composite solution to the microneedle structure mold cavity; d) drying the composite solution to form a microneedle structure; and e) removing the microneedle structure from the microneedle structure mold.

In a fourth aspect, a method is disclosed for producing a microneedle structure. The steps of this method include a) combining at least one drug or biomolecule with at least one nanomaterial to form a nanomedicine; b) forming a composite solution comprising at least one dissolvable polymer and the nanomedicine, wherein said nanomedicine is well-dispersed throughout said composite solution; c) adding the composite solution to the surface of a microneedle structure mold; d) forcing the composite solution to the microneedle structure mold cavity; e) drying the composite solution to form a microneedle structure; and f) removing the microneedle structure from the microneedle structure mold.

In a fifth aspect, a method is disclosed for producing a microneedle structure of increased mechanical strength. The steps of this method include a) combining at least one drug or biomolecule with at least one nanomaterial to form a nanomedicine; b) forming a composite solution comprising at least one dissolvable polymer and the nanomedicine, wherein said nanomedicine is well-dispersed throughout said composite solution; c) adding the composite solution to the surface of a microneedle structure mold; d) forcing the composite solution to the microneedle structure mold cavity; e) drying the composite solution to form a microneedle structure; and f) removing the microneedle structure from the microneedle structure mold.

In a sixth aspect, a method is disclosed for delivering a drug or biomolecule transdermally or to the epithelia. The steps of this method include applying a biocompatible, dissolvable microneedle structure to the skin or epithelia of a subject. The microneedle structure includes a plurality of microneedles. Each of the microneedles is comprised of at least one dissolvable polymer, the drug or biomolecule, and a nanomaterial, wherein the nanomaterial is well-dispersed throughout each of the microneedles. The application should be such that the microneedles of the microneedle structure penetrate the skin or epithelia and the drug or biomolecule is released upon the dissolution of the microneedles. In some embodiments, the dissolution of the microneedles substantially occurs within five minutes of the penetration of the skin or epithelia.

In a seventh aspect, a method is disclosed for delivering a drug or biomolecule to the cytoplasm and/or nucleus of a cell within skin or epithelia. The steps of this method include applying a biocompatible, dissolvable microneedle structure to the skin or epithelia of a subject. The microneedle structure includes a plurality of microneedles. Each of the microneedles is comprised of at least one dissolvable polymer, the drug or biomolecule, and a nanomaterial, wherein the nanomaterial is well-dispersed throughout each of the microneedles. The application should be such that the microneedles of the microneedle structure penetrate the skin or epithelia and the drug or biomolecule is released upon the dissolution of the microneedles. In some embodiments, the nanomaterial contains drug or biomolecule, as a nanomedicine, for drug or biomolecule delivery. In some embodiments, the dissolution of the microneedles substantially occurs within five minutes of the penetration of the skin or epithelia.

These and other objects, features and advantages of this disclosure will become apparent from the following detailed description of the various aspects of the invention taken in conjunction with the accompanying drawings.

BRIEF DESCRIPTION OF THE DRAWINGS

FIG. 4a and FIG. 4b are representative SEM images of silicon microneedle male molds used to prepare PDMS female molds for polymer microneedle fabrication. FIG. 4c and FIG. 4d show typical SEM images of dissolving polymer microneedles according to an embodiment of the invention.

DETAILED DESCRIPTION OF THE INVENTION

Figure 1:
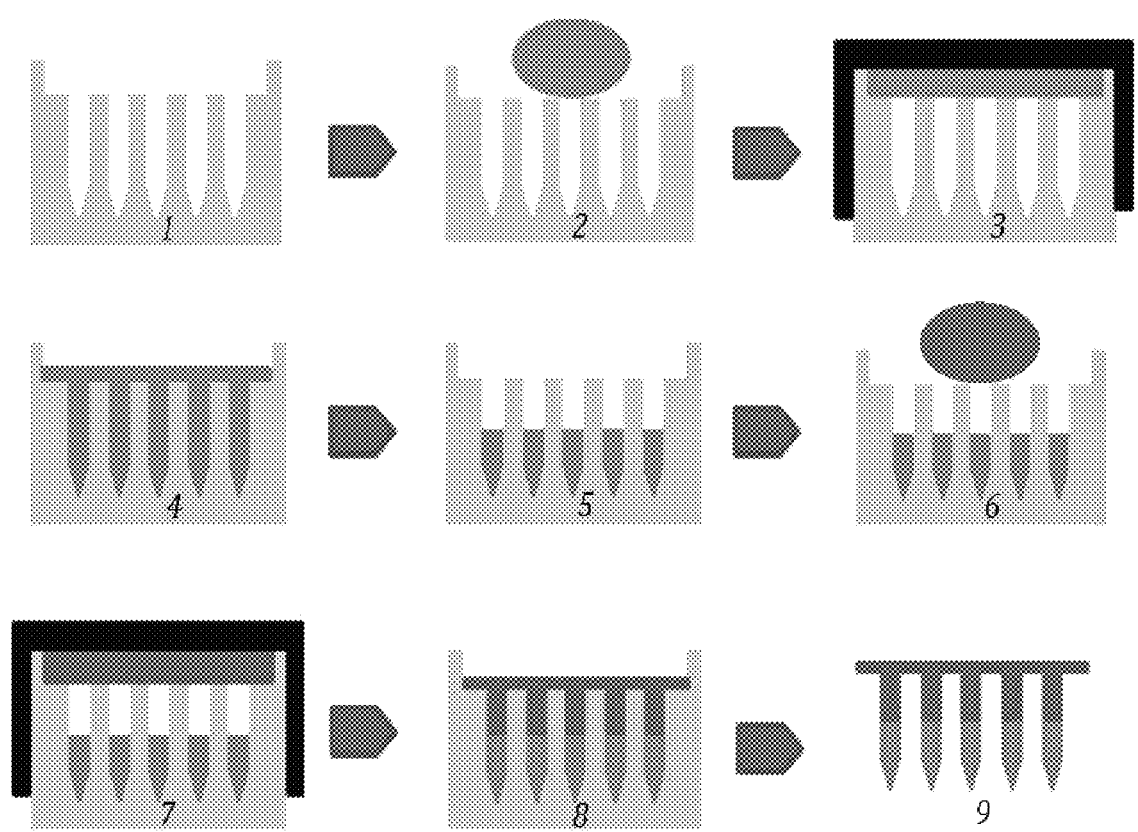
FIG. 1 depicts steps to manufacture one embodiment of a dissolving nanocomposite microneedle structure.

In a first aspect, a microneedle structure is disclosed comprising a plurality of microneedles, wherein each of the microneedles is comprised of at least one dissolvable polymer and a nanomaterial, wherein the nanomaterial is well-dispersed throughout each of the microneedles.

The microneedle structure comprises a plurality of microneedles connected by a base. The base serves to anchor the microneedles, allowing the microneedles to be removed from the microneedle structure mold and to be applied to a subject as one unit. One such embodiment of a microneedle structure can be seen in FIG. 1.

The nanomaterial may be any material in which at least one of the dimensions of the material is equal to or less than 100 nm, that is, 1 nm to 100 nm. In some embodiments, the nanomaterial possesses a positive charge on at least one of its surfaces. In some embodiments, the nanomaterial is comprised of nanoparticles. Nanomaterials may include nanoparticles, nanosheets, nanofibers, nanowires, nanotubes, or combinations thereof.

In some embodiments, the nanomaterial used comprises layered double hydroxide (LDH) nanoparticles. LDH nanoparticles possess high biocompatibility, a high aspect ratio (lateral size over thickness), and low cost. These LDH nanoparticles may be comprised of at least one of magnesium, aluminum, iron, cobalt, zinc, calcium or manganese. That is, any one of or combination of magnesium, aluminum, iron, cobalt, zinc, calcium or manganese may be used. For instance, in some embodiments, the LDH nanoparticles are comprised of magnesium and aluminum. In some embodiments, the LDH nanoparticles are comprised of zinc and aluminum. In some embodiments, the LDH nanoparticles are comprised of calcium and aluminum. In some embodiments, the LDH nanoparticles are comprised of nickel and aluminum. In some embodiments, the LDH nanoparticles are comprised of zinc and chromium. In some embodiments, the LDH nanoparticles are comprised of zinc and iron. In some embodiments, the LDH nanoparticles are comprised of magnesium and iron. In some embodiments, the LDH nanoparticles are comprised of calcium and iron. In some embodiments, the LDH nanoparticles are comprised of zinc and cobalt. In some embodiments, the LDH nanoparticles are comprised of magnesium, calcium and iron. In some embodiments, the LDH nanoparticles are comprised of magnesium, calcium and aluminum.

In some embodiments, the polymer is biodegradable. The environment in which such degradation occurs will be within the skin or the epithelia of a subject. The nanomaterial used increases the mechanical strength of the dissolvable polymer without sacrificing the dissolution rate of the polymer within the skin or epithelia. In some embodiments, the dissolution rate of the microneedle structure containing the nanomaterial is within 25% of the dissolution rate of a comparable microneedle structure that does not include the nanomaterial. As a non-limiting example, a microneedle structure comprised of CMC, LDH nanoparticles and a drug will have a dissolution rate in the skin or epithelium that is no more than 25% faster or slower than that of a microneedle structure comprised only of CMC and the drug (i.e., no LDH nanoparticles). In some embodiments, the dissolution rate of the microneedle structure containing the nanomaterial is within 10% of the dissolution rate of a comparable microneedle structure that does not include the nanomaterial. In some embodiments, the dissolution rate of the microneedle structure containing the nanomaterial is within 1% of the dissolution rate of a comparable microneedle structure that does not include the nanomaterial.

In some embodiments, the nanomaterial has interaction with the polymer, for instance, covalent bonding, electrostatic interaction and/or hydrogen bonding. This interaction aids in allowing the nanomaterial to be distributed well in the polymer. In some embodiments, the polymer comprises negatively charged functional groups. When the polymer is negatively charged in solution, it may be incorporated into the internal layers of the nanomaterial having positive charge on at least one of its surfaces. This may allow the nanomaterial to disperse uniformly throughout the polymer. This consistent dispersion of the nanomaterial leads to enhanced mechanical properties of the microneedle structure. In some embodiments, the polymer is sodium carboxymethylcellulose (CMC).

As opposed to engineering plastics, nanomaterial strengthened polymer, such as LDH strengthened CMC, dissolves in water very rapidly while engineering plastics generally do not dissolve in water or take months to years to dissolve. The combination of the polymer and the nanomaterial has a higher elastic modulus than does the polymer without the addition of the nanomaterial. In some embodiments, the addition of the nanomaterial increases the elastic modulus between 50% and 500% over that of the pure polymer. In some embodiments, the addition of the nanomaterial increases the elastic modulus between 100% and 400% over that of the pure polymer. In some embodiments, the addition of the nanomaterial increases the elastic modulus between 150% and 400% over that of the pure polymer. In some embodiments, the addition of the nanomaterial increases the elastic modulus between 200% and 400% over that of the pure polymer. In some embodiments, the addition of the nanomaterial increases the elastic modulus between 250% and 350% over that of the pure polymer.

The composite solution used to form microneedle structures of increased mechanical strength includes at least one dissolvable polymer and at least one nanomaterial. In some embodiments, layered double hydroxide nanoparticles are present in a concentration between 0.5 wt % and 20 wt % relative to the mass of said polymer in the composite solution. In some embodiments, the layered double hydroxide nanoparticles are present in a concentration between 0.5 wt % and 15 wt % relative to the mass of said polymer in the composite solution. In some embodiments, the layered double hydroxide nanoparticles are present in a concentration between 1 wt % and 10 wt % relative to the mass of said polymer in the composite solution. In some embodiments, the layered double hydroxide nanoparticles are present in a concentration between 2 wt % and 15 wt % relative to the mass of said polymer in the composite solution. In some embodiments, the layered double hydroxide nanoparticles are present in a concentration between 2 wt % and 10 wt % relative to the mass of said polymer in the composite solution. In some embodiments, the layered double hydroxide nanoparticles are present in a concentration between 2 wt % and 5 wt % relative to the mass of said polymer in the composite solution.

In some embodiments, the dissolvable polymer is present in a concentration between 0.5 wt % and 99.5 wt % relative to the mass of solvent in the solution. In some embodiments, the dissolvable polymer is present in a concentration between 2 wt % and 90 wt % relative to the mass of solvent in the solution. In some embodiments, the dissolvable polymer is present in a concentration between 2 wt % and 50 wt % relative to the mass of solvent in the solution. In some embodiments, the dissolvable polymer is present in a concentration between 2 wt % and 10 wt % relative to the mass of solvent in the solution. In some embodiments, the dissolvable polymer is present in a concentration between 20 wt % and 90 wt % relative to the mass of solvent in the solution. In some embodiments, the dissolvable polymer is present in a concentration between 1 wt % and 50 wt % relative to the mass of solvent in the solution. In some embodiments, the dissolvable polymer is present in a concentration between 20 wt % and 50 wt % relative to the mass of solvent in the solution. In some embodiments, the dissolvable polymer is present in a concentration between 40 wt % and 90 wt % relative to the mass of solvent in the solution. In most embodiments, the solvent is water or water-based.

In some embodiments, the microneedles may further comprise at least one drug or biomolecule. In some embodiments, the drug or biomolecule is negatively charged. The drug or biomolecule is released into the skin or epithelia upon dissolution of the polymer.

In addition to its mechanical strengthening function, the nanomaterial (such as LDH) can also help large molecules such as DNA and siRNA to penetrate membranes to enter cells. DNA and siRNA cannot penetrate cell membranes by simple diffusion but they must enter cells in order to be functional. As the microneedles are applied to the skin or epithelia, these large molecules will also be released upon polymer dissolution. This microneedle structure can also be utilized in situations wherein controlled release is important; the speed of dissolution can be controlled by adjusting the composition and concentration of the polymer and the nanomaterial. Further, the nanomaterial structure can assist in improving the stability of drugs and biomolecules by providing protection upon injection into the skin or epithelia. In some embodiments, the drug or biomolecule may be associated with the nanomaterial to form a nanomedicine. In these embodiments, the drug or biomolecule may be released into the skin or epithelia of the subject, or into the cytoplasm and/or nucleus of a cell within skin or epithelia, with or without the associated nanomaterial. A drug or biomolecule is considered to "be associated with" the nanomaterial by, for instance, covalent bonding, electrostatic attraction, or hydrogen bonding, or by loading the drug or biomolecule to the internal cavity of the nanomaterial.

In some embodiments, the microneedles are comprised of layered double hydroxide nanoparticles comprising a positive charge on at least one surface; polymer comprising negatively charged functional groups; and a drug or biomolecule.

In some embodiments, the average radius of the tips of the microneedles is between 50 nanometers and 2 micrometers. In some embodiments, the average radius of the tips of the microneedles is between 50 nanometers and 1 micrometer. In some embodiments, the average radius of the tips of the microneedles is between 50 nanometers and 750 nanometers. In some embodiments, the average radius of the tips of the microneedles is between 50 nanometers and 500 nanometers. In some embodiments, the average radius of the tips of the microneedles is between 50 nanometers and 250 nanometers. In some embodiments, the average radius of the tips of the microneedles is between 50 nanometers and 100 nanometers.

The shape of each microneedle is not limited, provided that adequate insertion into the skin or epithelia is achieved. In some embodiments, the shape of each microneedle is pyramidal. In other embodiments, the shape of each microneedle is conical. In still other embodiments, the shape of the tip of each microneedle is chiseled or beveled.

The aspect ratio is defined as the ratio between the height of a microneedle and the width (at the base) of the same microneedle. In some embodiments, the microneedles have an aspect ratio between 1 and 200. In other embodiments, the aspect ratio is between 1 and 100. In some embodiments, the aspect ratio is between 1 and 50. In yet other embodiments, the aspect ratio is between 1 and 10. In other embodiments, the aspect ratio is between 1 and 5. In other embodiments, the aspect ratio is between 1 and 3. In other embodiments, the aspect ratio is between 2 and 10. In other embodiments, the aspect ratio is between 2 and 5.

In some embodiments, the average height of the microneedles of the microneedle structure is between 10 and 1000 µm. In some embodiments, the average height of the microneedles of the microneedle structure is between 100 and 500 µm. In some embodiments, the average height of the microneedles of the microneedle structure is between 100 and 300 µm. In some embodiments, the average height of the microneedles of the microneedle structure is between 100 and 200 µm. In some embodiments, the average height of the microneedles of the microneedle structure is between 150 and 300 µm. In some embodiments, the average height of the microneedles of the microneedle structure is between 150 and 250 µm. In some embodiments, the average height of the microneedles of the microneedle structure is between 150 and 200 µm. In some embodiments, the average height of the microneedles of the microneedle structure is between 60 and 300 µm. In some embodiments, the average height of the microneedles of the microneedle structure is between 125 and 175 µm.

Width, for the purpose of this disclosure, is defined as the straight line distance between the two widest points of a microneedle at the base of the microneedle structure; this would include the diameter of a substantially conical microneedle. In some embodiments, the average width of the bottom of the microneedles of the microneedle structure is between 5 and 500 µm. In some embodiments, the average width of the microneedles of the microneedle structure is between 10 and 300 µm. In some embodiments, the average width of the microneedles of the microneedle structure is between 10 and 200 µm. In some embodiments, the average width of the microneedles of the microneedle structure is between 10 and 100 µm. In some embodiments, the average width of the microneedles of the microneedle structure is between 10 and 50 µm. In some embodiments, the average width of the microneedles of the microneedle structure is between 20 and 50 µm. In some embodiments, the average width of the microneedles of the microneedle structure is between 20 and 100 µm. In some embodiments, the average width of the microneedles of the microneedle structure is between 50 and 200 µm. In some embodiments, the average width of the microneedles of the microneedle structure is between 50 and 100 µm.

In some embodiments, the density of microneedles of the microneedle structure is between 1,000 and 20,000 $cm^{-2}$. In some embodiments, the density of microneedles of the microneedle structure is between 10,000 and 20,000 $cm^{-2}$. In some embodiments, the density of microneedles of the microneedle structure is between 5,000 and 10,000 $cm^2$. In some embodiments, the density of microneedles of the microneedle structure is between 10,000 and 15,000 $cm^{-2}$. In some embodiments, the density of microneedles of the microneedle structure is between 11,000 and 12,000 $cm^{-2}$. In some embodiments, the density of microneedles of the microneedle structure is between 1,000 and 5,000 $cm^2$. In some embodiments, the density of microneedles of the microneedle structure is between 5,000 and 20,000 $cm^{-2}$. In some embodiments, the density of microneedles of the microneedle structure is between 1,000 and 10,000 $cm^{-2}$.

The height, width and density of the microneedles of the microneedle structure are to be such that the majority of the microneedles are strong enough to achieve adequate insertion into the skin or epithelia. Mechanically strengthened dissolving polymers are useful for fabricating densely packed, small microneedles for drug delivery, which enhances the immune response. Microneedles of greater height may require a greater width, depending on the density of the microneedles on the microneedle structure. The person of skill will be able to determine the necessary relationship between height, width and density without undue experimentation.

In some embodiments, a method for producing a microneedle structure is disclosed. In some embodiments, this microneedle structure possesses increased mechanical strength over that of a microneedle structure comprised of the polymer alone, i.e., without the nanomaterial. In this method, a composite solution comprising at least one dissolvable polymer and a nanomaterial is formed. In some embodiments, the nanomaterial comprises layered double hydroxide nanoparticles comprising a positive charge on at least one surface and the polymer comprises negatively charged functional groups. In some embodiments, the composite solution may also include one or more drugs or biomolecules, as described above. In yet other embodiments, a nanomedicine is formed by combining at least one drug or biomolecule with a nanomaterial. In some embodiments, the drug or biomolecule is negatively charged. In these embodiments, the formation of the composite solution includes combining this nanomedicine with at least one dissolvable polymer. It is advantageous for the components of the composite solution to be well-dispersed and for the nanomaterial to be substantially homogenously distributed in the polymer.

The composite solution is then added to the surface of a microneedle structure mold. The composite solution is then forced into the cavity of the microneedle structure mold. In some embodiments, the composite solution may be forced into the cavity by centrifuging the microstructure needle mold. In other embodiments, a vacuum may be used to force the composite solution into the cavity of the microstructure needle mold. After the forcing step has been completed, any composite solution remaining on the surface of the microstructure needle mold (that is, where the composite solution is initially applied) may be removed in order to minimize material waste. However, in some embodiments, it is advantageous to retain some composite solution on the surface of the microstructure needle mold so that the microneedles are connected together. The composite solution contained in the microstructure needle mold cavity is then dried in order to form a microneedle structure. In some embodiments, the drying step may occur at the same time as the forcing step, for instance, if the forcing step is performed in vacuum or with other methods such as microwave to dry the composite solution. In some embodiments, it may be desirable to repeat the steps of adding composite solution, forcing the composite solution into the cavity of the microneedle structure mold, and drying the composite solution in order to form a microneedle structure; this repeating of steps may occur one or more times. The repeating of steps may allow for the layering of the same composite solution or different solutions which may contain different constituents in each layer. In some embodiments, one may make a "single layer" microneedle structure, in which all steps are completed in one round with one composite solution, such that the microneedles and the base of the microneedle structure are all comprised of the same composite solution. In some embodiments, the steps may be repeated more than one time, but with the same composite solution in each round of steps. In these embodiments, the first layer of the composite solution may be added, forced, and dried in the microneedle structure mold cavity, then more composite solution may be added to form the microneedle structure base. In other embodiments, the microneedle structure may be multilayered. In these embodiments, the steps may be repeated using a different composite solution in each layer or using the pure polymer solution (i.e., with no nanomaterial or drug) in certain layers. For instance, in some embodiments, after the microneedles are formed by using one or more composite solutions, it may be desirable to add more composite solution or, alternatively, pure polymer solution to form the base of the microneedle structure. The microneedle structure is then removed from the microneedle structure mold. One such embodiment of a method for producing a microneedle structure is shown in FIG. 1 and described more fully below.

In some embodiments, the microneedle structure is produced at a temperature between about 4° C. and 37° C. In some embodiments, the microneedle structure is produced at a temperature between about 20° C. and 37° C. In some embodiments, the microneedle structure is produced at a temperature between about 4° C. and 25° C. In some embodiments, the microneedle structure is produced at a temperature between about 20° C. and 25° C.

The nanomaterials in the microneedle structure described herein may be multifunctional, in that the addition of the nanomaterial to the polymer not only increases the mechanical strength of the polymer (and thus the microneedles), but also allows the microneedles to deliver drugs or biomolecules effectively that may otherwise not be able to enter cells. Therefore, in some embodiments, the nanomaterials may contain drug or molecule to serve more than one function: they enhance the mechanical properties of the microneedle by improving the strength of the polymer and they act as nanomedicine when the nanomaterials are associated with a drug or biomolecule. In some embodiments, a method for delivering a drug or biomolecule to the epithelia or transdermally is disclosed. For purposes of this disclosure, transdermal includes the traditional definition of "through the skin", while epithelial delivery includes the application of the microneedle structure to any accessible epithelia, including the epithelia of the mouth. For instance, the microneedle structure disclosed herein could also be used for injecting a local anesthetic into the tissue surrounding a tooth. The steps of this method include applying a biocompatible, dissolvable microneedle structure to the skin or epithelia of a subject. The microneedle structure includes a) at least one dissolvable polymer, b) the drug or biomolecule to be delivered and c) a nanomaterial which is well-dispersed throughout each of the microneedles. The application of the microneedle structure should be such that the microneedles of the microneedle structure penetrate the skin or epithelia and the drug or biomolecule is released upon the dissolution of the microneedles. In some embodiments, the drug or biomolecule may be associated with the nanomaterial to form a nanomedicine; in these embodiments, the nanomedicine is released upon the dissolution of the microneedles. In some embodiments, the dissolution of the microneedles substantially occurs within five minutes of the penetration of the skin or epithelia. In some embodiments, the dissolution of the microneedles substantially occurs within one minute of the penetration of the skin or epithelia. In some embodiments, the microneedles are comprised of layered double hydroxide nanoparticles comprising a positive charge on at least one surface and a dissolvable polymer comprising negatively charged functional groups.

In some embodiments, a method is disclosed method for delivering a drug or biomolecule to the cytoplasm and/or nucleus of a cell within skin or epithelia. This is especially useful for delivering those drug molecules or biomolecules to the cytoplasm and/or nucleus of cells within skin or epithelia which otherwise would be unable to enter the cells. These molecules are often not able to penetrate a cell membrane due to various reasons such as size, instability, hydrophilicity, or negative surface charge.

The steps of this method include applying a biocompatible, dissolvable microneedle structure to the skin or epithelia of a subject. The microneedle structure includes a) at least one dissolvable polymer, b) the drug or biomolecule to be delivered and c) a nanomaterial which is well-dispersed throughout each of the microneedles. The application of the microneedle structure should be such that the microneedles of the microneedle structure penetrate the skin or epithelia and the drug or biomolecule is released upon the dissolution of the microneedles. In some embodiments, the drug or biomolecule may be associated with the nanomaterial to form a nanomedicine; in these embodiments, the nanomedicine is released upon the dissolution of the microneedles. In some embodiments, the dissolution of the microneedles substantially occurs within five minutes of the penetration of the skin or epithelia. In some embodiments, the dissolution of the microneedles substantially occurs within one minute of the penetration of the skin or epithelia. In some embodiments, the microneedles are comprised of layered double hydroxide nanoparticles comprising a positive charge on at least one surface and a dissolvable polymer comprising negatively charged functional groups.

The mechanical strength of the microneedle is increased over what it would be with the polymer alone when the nanomaterial is well-dispersed. "Well-dispersed", for purposes of this disclosure, does not necessarily mean uniformly distributed. While good dispersion is desired, the distribution of nanomaterial does not need to be uniform throughout the microneedle in order to obtain the desired results. Well-dispersed, but non-uniformly distributed, nanomaterial will still lead to optimized properties. In contrast, a microneedle in which the nanomaterial is located substantially at or near the tip of the microneedle would not possess the desired increase in mechanical strength found when the nanomaterial is located throughout the entirety of the microneedle. The same is true whether or not a drug or biomolecule is associated with the nanomaterial, such as with the formation of a nanomedicine, as described supra. As demonstrated in the example below, good dispersion of the nanomaterial in the composite solution phase (with the polymer) leads to increased strength of the resulting microneedle structure.

ABBREVIATIONS

The following abbreviations and terms have the indicated meanings throughout:
APCs=antigen-presenting cells
CMC=carboxymethylcellulose sodium salt
DMSO=dimethyl sulfoxide
LDH=layered double hydroxide
PBS=phosphate buffered saline
PDMS=polydimethylsiloxane
PVP=polyvinylpyrrolidone
UV=ultraviolet Experimental Details Materials: NaOH, $MgCl_2$ and $AlCl_3$ were obtained from International Laboratory USA. CMC (Mw 90,000), phosphate buffered saline (PBS), dimethyl sulfoxide (DMSO) and Hoechst 33342 were purchased from Sigma-Aldrich (Castle Hill, NSW, Australia). Dextran Fluorescein (Mw 70,000) was from Life Technologies Corporation (Hong Kong). All materials were used without further purification.

Preparation of $Mg_2Al$-LDH nanoparticles: $Mg_2Al$-LDH nanoparticles were prepared according to the method described by Xu et al. (Z. P. Xu, G. Stevenson, C. Lu, G. Q. Lu, Dispersion and size control of layered double hydroxide nanoparticles in aqueous solutions, J. Phys. Chem. B 110 (2006) 16923-16929; and Z. P. Xu, G. Stevenson, C. Lu, G. Lu, P. Bartlett, P. Gray, Stable suspension of layered double hydroxide nanoparticles in aqueous solution, J. Am. Chem. Soc. 128 (2006) 36-37). Briefly, 40 ml of 0.15M NaOH solution was mixed with 10 ml of solution containing 2.0 mmol of $MgCl_2$ and 1.0 mmol of $AlCl_3$ under vigorous stirring. The container was sealed and the solution was under stirring for 10 minutes. Next, the solution was centrifuged and washed once with water. The obtained slurry was dispersed in 40 ml of water and hydrothermally treated at 80° C. for 4 hours in an airtight container. The concentration of LDH is about 0.4 wt %. The mass of LDH was determined by weighing the LDH mass collected from suspension.

Fabrication of CMC-LDH nanocomposites: LDH solutions with different concentrations were mixed with CMC powder to make composite solution. Briefly, 10 ml of LDH solutions with different concentrations were mixed with 200 mg of CMC to prepare composite solution followed by placing in fume hood and drying to obtain polymer nanocomposite. The prepared nanocomposites contained 2 wt %, 5 wt % and 10 wt % LDH nanoparticles. The weight percentage is the mass ratio of LDH nanoparticles to CMC. During microneedle fabrication, CMC-LDH solution was centrifuged onto the mold at 3000×g for 10 minutes. To mimic this process, for another batch of samples, 10 ml of solution containing 25 mg LDH nanoparticles was mixed with 500 mg of CMC and the mixture was sonicated for 30 minutes. After that, the solution was centrifuged for 10 min at 4000×g. The amount of the nanoparticles which were centrifuged to the bottom of solution was trivial. The upper layer of solution was collected and sonicated for 30 minutes for being used to make nanoindentation samples and microneedle arrays.

Figure 2:
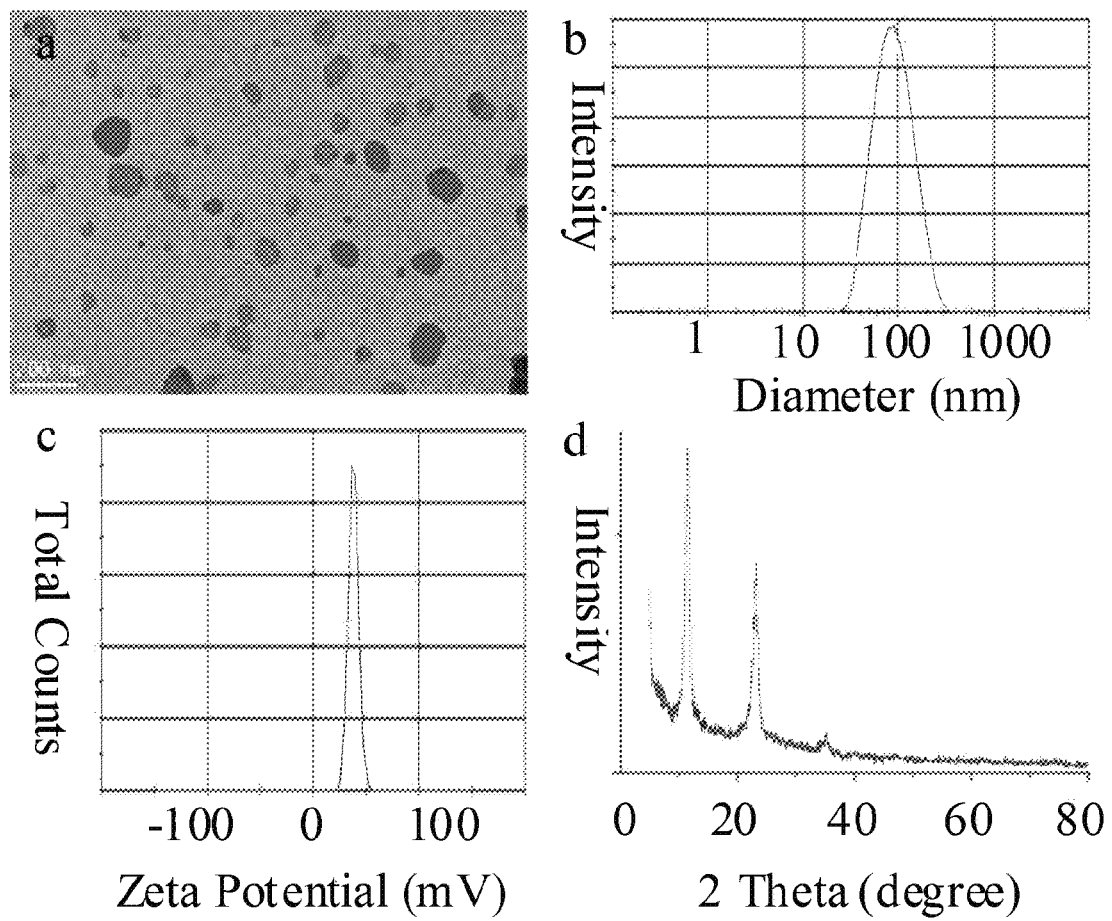
FIG. 2 depicts various measurements and characteristics of nanoparticles according to an embodiment of the invention. a) High-resolution transmission electron microscopy image of well dispersed nanoparticles. b) Particle size distribution of suspension containing nanoparticles. c) The zeta potential of nanoparticles in aqueous and buffer-free solution. d) X-ray diffraction pattern of pristine nanoparticles.
Figure 3:
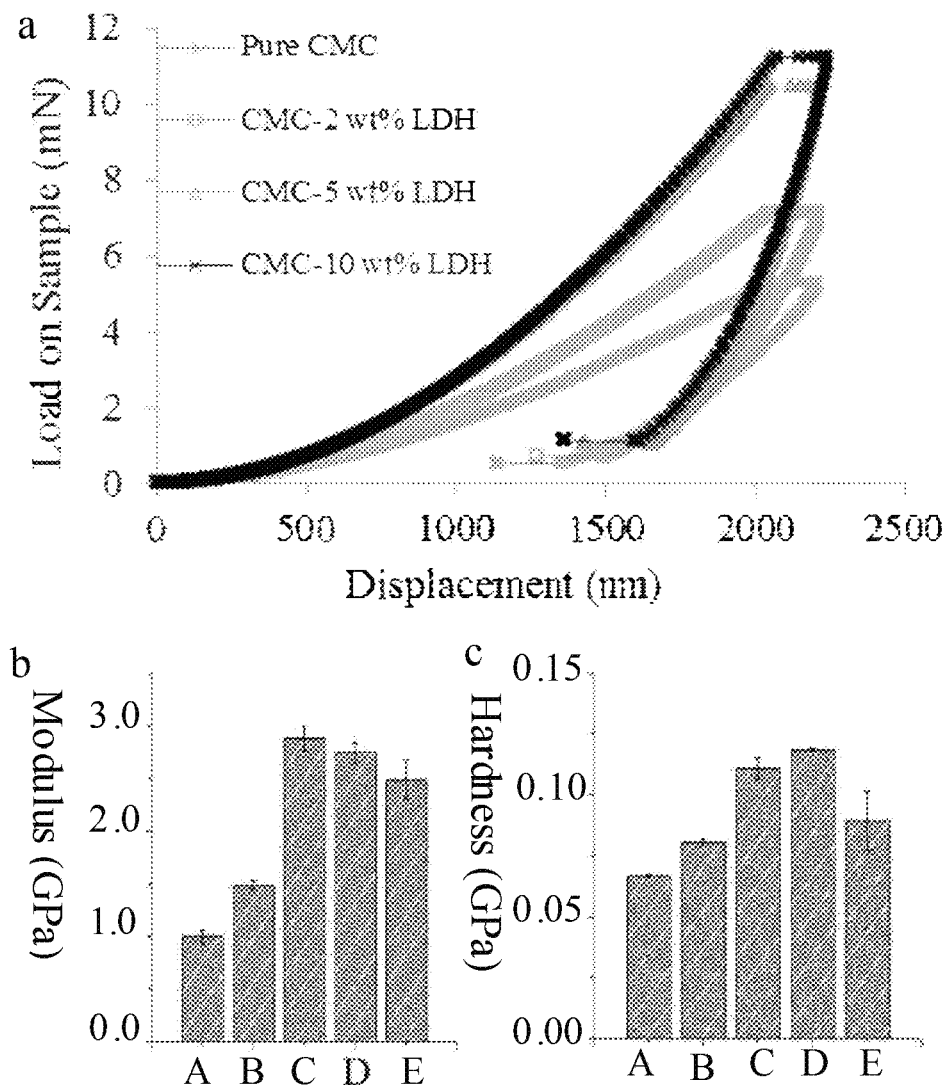
FIG. 3 depicts various measurements and characteristics of nanoparticles according to an embodiment of the invention. a) Load-displacement curves from nanoindentation. b) Elastic modulus and c) Hardness of CMC polymer films with different nanoparticle concentrations.
Figure 4:
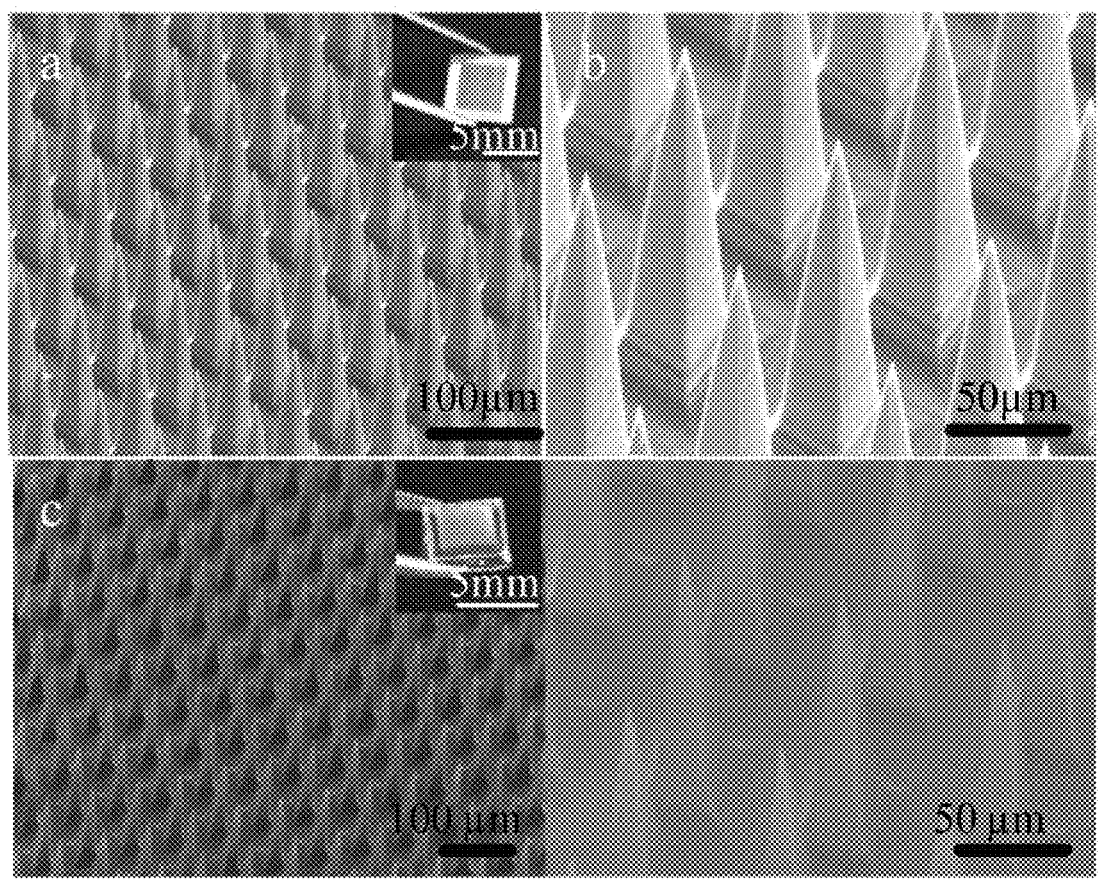
FIG. 4 shows scanning electron microscopy images.

Fabrication of microneedle patches: Silicon microneedle arrays were used as male mold. The arrays were fabricated according to methods described in literature (See, for instance, R. Bhandari, S. Negi, F. Solzbacher, Wafer-scale fabrication of penetrating neural microelectrode arrays, Biomed. Microdevices 12 (2010) 797-807). Briefly, a silicon wafer was diced by a diamond blade to create silicon microcolumns of required dimension and spacing. A two-step isotropic etching using a mixture of nitric acid and hydrofluoric acid was used to fabricate sharp microneedles. This silicon microneedle array male mold was washed with ethanol for 3 times and dried in air and then PDMS was slowly poured over the surface of silicon microneedle array. The silicon microneedle array male mold immersed in PDMS was placed in a fume hood for curing for 24 hours. After curing, the silicon microneedle array male mold was peeled off and the PDMS female mold was washed with water and ethanol for 3 times before casting. FIG. 1 shows the steps to manufacture a dissolving polymer microneedle patch. FIG. 1-1 shows the PDMS mold. To make microneedle patches, firstly, 30 µl of LDH-CMC composite solution was added to the surface of mold (FIG. 1-2). Then the mold was sealed (FIG. 1-3) and centrifuged at 3000×g for 10 minutes. After centrifugation, the solution remaining on the surface of the mold was collected by pipette and the mold was placed in a fume hood to dry for 30 minutes. During the drying period, a solid microneedle tip was fabricated (FIG. 1-5). Subsequently, 40 µl of LDH-CMC composite solution was added to the surface (FIG. 1-6) and the mold was sealed (FIG. 1-7) and centrifuged for 10 minutes. Finally, 200 µl of LDH-CMC composite solution was added to the surface of centrifuged mold and placed in a fume hood for drying. After 8 hours, the mold was placed in a sealed desiccator. When the microneedle patch was dried completely, it was removed from the mold (FIG. 1-9) and stored in a desiccator until use.

Characterization of mechanical properties of nanocomposites and morphology of microneedle patches: Nanoindentation was carried by a MTS Nano Indenter XP® (MTS Cooperation, Nano Instrument Innovation Center, NT) with three-sided pyramid (Berkovich) diamond indenter. The indenter was pressed into materials with constant strain rate (0.05 l/s) from the sample surface into 2000 nm deep. The fabricated polymer microneedle patch was observed by scanning electron microscope (JEOL JSM-820 and FEG-SEM JEOL JSM-6335 F). The samples were tilted 45° for SEM.

Cell lines and culture conditions: Human lung epithelium adenocarcinoma cells (A549) and human cervical carcinoma (HeLa) cells were cultured in Dulbecco's Modified Eagle Medium (DMEM) High Glucose supplemented with 10% fetal bovine serum and 1% penicillin/streptomycin. Cells were maintained at 37° C. in a humidified atmosphere containing 5% $CO_2$. Cells were grown in tissue culture flasks. After over 80% confluent, the cells were trypsinized and washed and cell suspension was plated into 96-well plate.

Cell viability test: A549 and HeLa cells were washed twice with trypsin-EDTA. Cells suspended in DMEM (with 10% FBS, 1% penicillin/streptomycin) were plated into 96-well plates at 2,000 cells per well. The cells were incubated at 37° C. for 48 h before treatment with LDH nanoparticles. Cells were incubated with various concentrations of LDH nanoparticles in 200 µL of DMEM (with 10% FBS, 1% penicillin/streptomycin) for an additional 72 h. The original medium in each well was subsequently removed. 160 µL of DMEM (without FBS) and 40 µL of MTT stock solution (5 mg/mL in PBS) were added and incubated for 4 h. The medium containing MTT was completely removed, followed by addition of 200 µL DMSO and 25 µL glycine buffer (0.1M glycine, 0.1M NaCl, pH 10.5) to each well. Cell viabilities were determined by reading the absorbance of the plates at 570 nm and 750 nm using a BioTek Powerwave XS microplate reader.

Confocal microscopy study of microneedle patches and their applications in human and pig skin: Excised pig ears were obtained from the local abattoir (Highchester Pty Ltd, Gleneagle, Australia). The ventral side of the ear was lightly shaved followed by thoroughly rinsing. The ventral skin (epidermis and dermis) was then separated from the ear (cartilage) using tweezers and scalpel. Excised human skin was obtained from abdominal plastic surgery patients. On arrival the adipose tissue was removed using a scalpel and the skin was rinsed. All patients signed an informed consent approved by the Princess Alexandra Hospital Research Committee approval no. 097/090 Skin (both pig and human) was stored at −20° C. prior to use. For microneedle application, the skin (pig or human) was thawed, rinsed, dried then pinned down taut on a covered corkboard. The tissue was stored on saline moistened gauze throughout the experiment when not in use. A microneedle array was then applied using a spring applicator for 1, 2 or 5 minutes (n=3 per skin type). After microneedle application, the treatment area was excised with an 8 mm biopsy and the tissue fixed in 1 mL 4% formaldehyde in methanol for 1 hour. Following fixing, the tissue was removed and washed 3 times for 10 minutes in 1 mL 0.1M phosphate buffered saline. The samples were then stored at 4° C. until imaging.

Reflectance confocal microscopy was done using a Vivascope® 1500 Multilaser (Lucid Inc., Rochester, N.Y., U.S.A). The protocol was adapted from a previously published procedure (E. M. T Wurm, C. Longo, C. Curchin, H. P. Soyer, T. W. Prow, G. Pellacani, In vivo assessment of chronological ageing and photoageing in forearm skin using reflectance confocal microscopy, Br. J. Dermatol. 167 (2012) 270-279). Briefly, a laser diode was used to excite the tissue at 830 nm. ImageJ (NIH, U.S.A) was used to analyze the images. Laser scanning confocal microscopy was done using a Zeiss LSM 510 Meta (Carl Zeiss Inc., Germany). Prior to imaging the tissue was stained with Hoechst 33342, a nuclei stain. A stock solution of 10 mg/mL Hoechst 33342 in dimethyl sulfoxide was prepared. A working solution was made by a 1:1000 dilution in 0.1M phosphate buffered saline. The tissue was incubated with the stain for 1 hour at room temperature followed by three washing steps for 10 minutes in 0.1M phosphate buffered saline. The wavelengths used to excite the FITC-dextran and Hoechst 33342 was 488 nm and 405 nm, respectively.

Results

Characterization of $Mg_2Al$—Cl-LDH nanoparticles: $Mg_2Al$—Cl-LDH nanoparticles with a mean size of 80 nm and zeta potential of +40 mV in aqueous and buffer-free solution (FIG. 2a-c) were prepared. The as-prepared aqueous suspension contained well-suspended LDH nanoparticles without aggregation (FIG. 2a-b). XRD pattern shows the typical feature of $Mg_2Al$—Cl-LDH nanoparticles (FIG. 2d). Diffraction peaks shown in the XRD pattern of pristine LDH nanoparticles correspond to the (003), (006) and (009) plane reflections of LDH.

Mechanical properties of CMC and CMC-LDH nanocomposites: Varying amounts of LDH were incorporated into 2 wt % CMC aqueous solution to test the strengthening effect of LDH nanoparticles on the mechanical properties of CMC. After the samples were dried, nanoindentation was used to measure their elastic modulus and hardness. FIG. 3a shows typical load-displacement curves of CMC polymer with different concentrations of LDH nanoparticles. The nanoindentation cycle consists of three periods: loading-holding-unloading. Loading forces were increased at constant velocity and the nanoindenter tip sank into materials during the loading period, which contributed to both elastic and plastic deformation. Strong materials require a high force to achieve the same penetration depth during the loading period. As can be observed from FIG. 3a, much greater load is required for penetration of the same depth as LDH nanoparticle concentration increases from 0 wt % to 2, 5 and 10 wt % (relative to the mass of CMC in the samples). Apparently, adding LDH nanoparticles into CMC can significantly enhance its resistance to indentation and make CMC-LDH composites much stronger than pure CMC. FIG. 3b and FIG. 3c show the elastic modulus and hardness of polymers, respectively, calculated from unloading. The elastic modulus of pure CMC is 0.993±0.065 GPa. The elastic modulus of 2 wt % of LDH loaded CMC increased to 1.489±0.036 GPa. With LDH concentration increased to 5 wt %, the elastic modulus reaches 2.878±0.123 GPa. The elastic modulus increased to 290% of that of pure CMC polymer when 5 wt % of LDH nanoparticles were added to CMC (p<0.001). When the LDH concentration was increased to 10 wt %, the elastic modulus of the nanocomposite started to decrease. It should be noted that the hardness of pure CMC polymer is 0.067±0.001 GPa. The addition of LDH nanoparticles to CMC increased the hardness of the composite material to 0.080±0.001 GPa, 0.111±0.004 GPa and 0.118±0.001 GPa for CMC composites with 2 wt %, 5 wt % and 10 wt % of LDH nanoparticles, respectively.

Based on these results, the CMC composite with 5 wt % LDH nanoparticles was chosen as the starting material for preparing microneedle arrays. Since centrifugation (3000×g for 10 minutes) was used to force the viscous polymer solution to fill in the tiny cavity of a microneedle PDMS mold, the concentration of CMC aqueous solution was increased to 5 wt % to avoid unequal LDH nanoparticle distribution within the centrifuged microneedles. When 5 wt % LDH (relative to the mass of CMC) was added to the 5 wt % CMC solution followed by centrifugation at 4000×g for 10 minutes, it was found by simply observing the mixture solution that a negligible amount of LDH nanoparticles were sedimented. The bottom layer of solution was discarded and supernatant was used for nanoindentation measurements. The results show that the elastic modulus of 5 wt % CMC/5 wt % LDH was 2.486±0.186 GPa. The value is slightly lower than the highest elastic modulus of the sample dried from the solution of 2 wt % CMC incorporating with 5 wt % LDH, but it is still much better than that of pure CMC (p<0.001). The suspension of 5 wt % CMC/5 wt % LDH was then used for fabricating microneedles.

Characterization of CMC and CMC-LDH microneedle patches: The validation of the hypothesis that incorporation of LDH nanoparticles into CMC could significantly increase the mechanical properties of the polymer supported the use of this nanofiller-improved polymer to fabricate and test microneedle arrays. FIG. 4a and FIG. 4b are representative SEM images of silicon microneedle male molds used to prepare PDMS female molds for polymer microneedle fabrication. The height and density of silicon microneedles are 218 μm and 11,900 projections $cm^{-2}$, respectively. FIG. 4c and FIG. 4d show typical SEM images of our dissolving polymer microneedles. The polymer microneedles had uniform morphology and geometry. The microneedles were pyramidal in shape and the tip radius is below 500 nm. The length of these fabricated polymer projections is 165±3 μm (n=20 projections). This indicates a 24±1% reduction in length in comparison with that of the microneedles of the male mold. This decrease is mainly due to the contraction and solidification of CMC based composite materials during drying.

Figure 5:
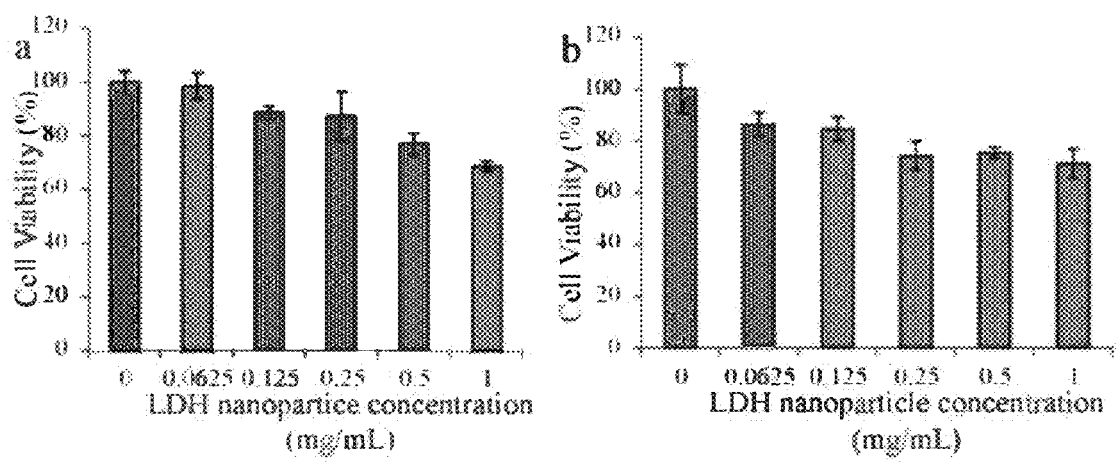
FIG. 5 shows the cytotoxicicity of nanoparticles against a) HeLa and d) A549 cell lines, respectively.
Figure 6:
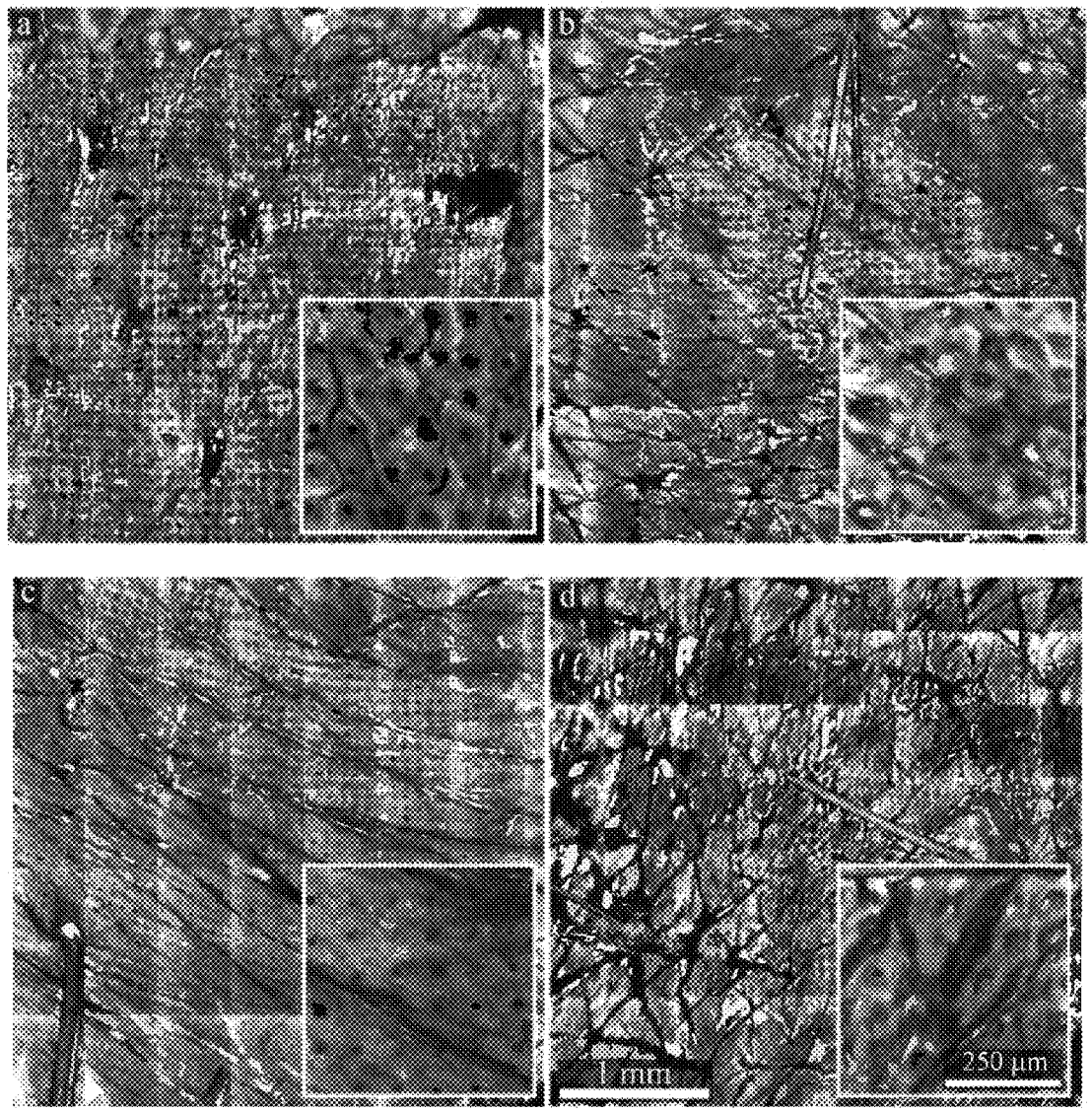
FIG. 6 depicts reflectance confocal microscopy images of skin after 5 minutes of microneedle application: a) pig skin after nanocomposite microneedle application, b) pig skin after control microneedle application, c) human skin after nanocomposite microneedle application, and d) human skin after control microneedle application.
Figure 7:
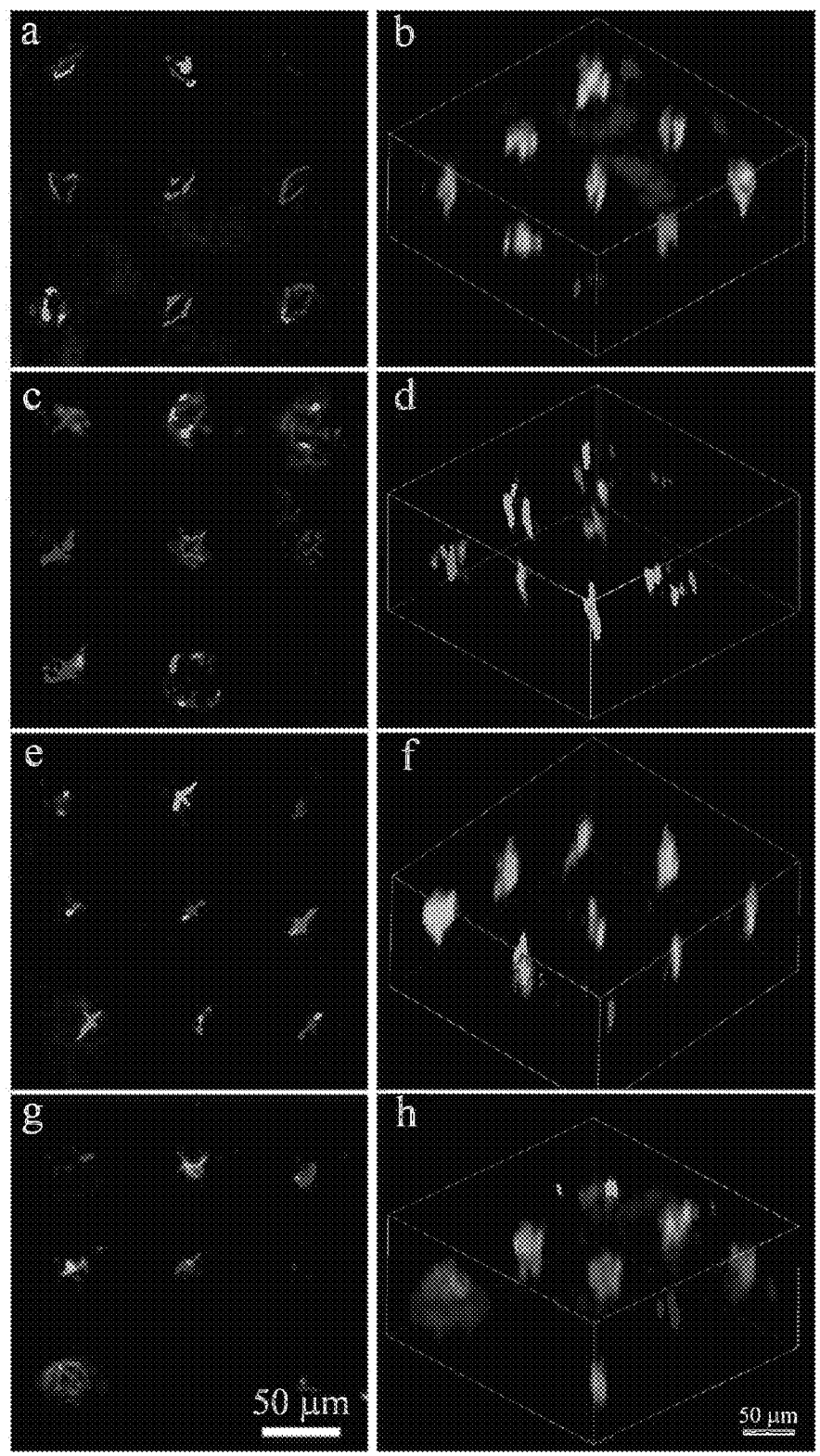
FIG. 7 shows laser scanning confocal microscopy images of skin after 5 minutes of microneedle application: a) and b) pig skin after nanocomposite microneedle application, c) and d) pig skin after control microneedle application, e) and f) human skin after nanocomposite microneedle application, and g) and h) human skin after control microneedle application.
Figure 8:
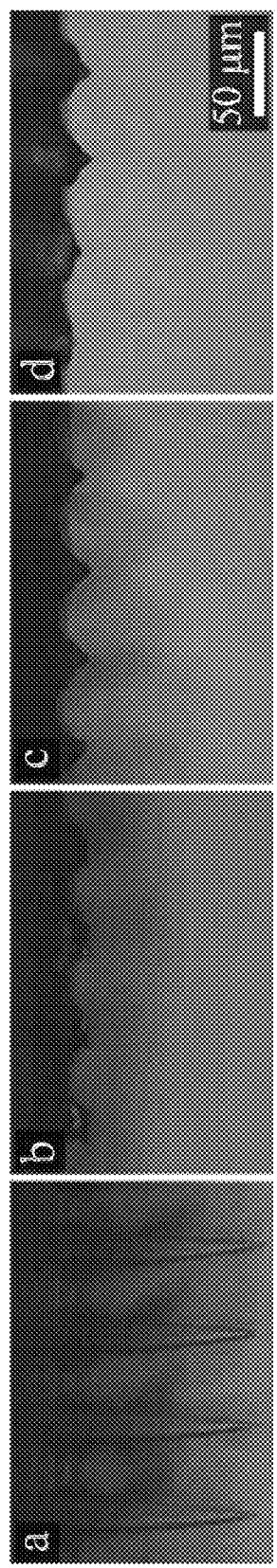
FIG. 8 shows merged fluorescence and reflectance confocal microscopy images of nanocomposite microneedles: a) before application, b) 1 minute, c) 2 minutes and d) 5 minutes after application to pig skin.

Cytotoxicity of CMC-LDH nanocomposite microneedle patches: Since nanomaterials were used in the material formulation for making microneedle arrays, before performing the in vivo test, the biocompatibility of the nanocomposite microneedle patches was investigated. Cytotoxicity of LDH nanoparticle reinforced composite microneedle patches against HeLa (FIG. 5a) and A549 (FIG. 5b) cells was measured by MTT assay (FIG. 5, at 72 hours post plating). The cell viability rate of nanocomposite treated cells was dose-dependent. Compared with the control group, when LDH nanoparticle concentration was increased from 0.0625 to 0.5 mg/ml, the cell viability remained over 80%. Even when LDH concentration was further increased to 1 mg/ml, both the HeLa and A459 cell viability were still over 70%.

Confocal microscopy study of the penetration and payload delivery of nanocomposite microneedle patches in human and pig skin: Once nanocomposite microneedle patches were successfully made, the next key question was whether these microneedles can reliably penetrate stratum corneum and deliver payload to skin. To perform this study, FITC-Dextran was simply mixed with CMC-LDH nanoparticle solution as a viewable drug and biomolecules surrogate and then cast onto the tips of microneedles; the nanofiller composite microneedle penetration was then tested in excised pig and human skin. To determine whether the microneedles can uniformly penetrate skin, reflectance confocal microscopy (RCM) was used to image both the treated pig skin and human skin (representative images shown in FIG. 6a-d). Nanocomposite microneedles applied to pig skin resulted in successful breaching of the stratum corneum and uniform penetration within the skin across the array (FIG. 6a). The penetration depth analyzed from the RCM images was 71±7 μm (n=40 projections). These results differed from what was observed for the CMC only microneedles where the penetration was not uniform (FIG. 6b). The center area shows penetration but no penetration holes are able to be clearly observed in the rest area. The depth of the penetration in the center area was found to be 46±12 μm (n=40 projections, $p<0.001$ between CMC and CMC-LDH microneedle penetration in pig skin). The nanocomposite microneedles also resulted in successful breaching and penetration into human skin (FIG. 6c) with a depth of 64±9 μm (n=40 projections). The CMC only microneedles resulted in indents on the skin surface with minimal penetration of 39±8 μm (n=40 projections, $p<0.001$ between CMC and CMC-LDH microneedle penetration in human skin) (FIG. 6d). Besides achieving apparent deeper penetration depth in both pig and human skin, CMC-LDH nanocomposite microneedles can be more reliable on successful application while CMC microneedles result in inconsistent penetration across the array, due to the microneedles sometimes bending on skin surface.

The RCM samples were then imaged using laser scanning confocal microscopy (LSCM) to determine payload dissolution and diffusion within the skin (representative images shown in FIG. 7a-h, after five minutes of microneedle application). For pure CMC microneedle applied skin samples, the images were selected from the area where penetration of microneedles into skin was achieved. The delivery sites are clearly observed from the top view of the skin samples (FIGS. 7a, 7c, 7e and 7g), which further confirms the polymer microneedles are able to pierce stratum corneum. The corresponding 3-D images (FIGS. 7b, 7d, 7f and 7h) demonstrate the microneedles dissolved in the skin and the FITC payload was delivered to thin layer beneath the skin surface. The CMC-LDH nanocomposite microneedles can reliably penetrate skin and deliver the payload into skin. Compared with CMC microneedles, the nanomaterial strengthened microneedles result in more consistent penetration within the skin across the whole patch area.

To investigate whether the mechanically strengthened microneedles can still rapidly dissolve in skin, the microneedles were observed before application in skin and at 1, 2 and 5 minutes after skin penetration. The results are shown in FIG. 8a-d. The figure shows the merged fluorescence and reflectance confocal microscopy images of microneedles before and after being applied to skin. Before application, the fluorescent payload can be clearly seen in green throughout the shaft of the microneedles (FIG. 8a). No fluorescence signal could be detected at the base of the array, which has the added benefit of reducing cost through conserving drug by reducing drug wastage. Because of this, minimal fluorescence was seen on the surface between the microneedles due to the payload being cast within the projections instead of being 'wasted' in the backing layer of the microneedles. After skin application, it can be seen that almost all of the microneedles are dissolved in the skin after only 1 minute. Quick dissolution within skin is crucial for a short administration time. For comparison, in a previous report, methacrylic acid (MAA) was copolymerized with vinyl pyrollidone (VP) to form poly(vinylpyrrolidone-co-methacrylic acid) (PVP-MAA) to improve the mechanical strength of the fabricated microneedles. However, with the addition of MAA, the dissolution rate of the microneedles greatly slowed. For example, PVP-MAA microneedles (25% MAA) need 2 hours to dissolve within porcine skin while at the same size pure PVP microneedles dissolve within 15 minutes.

The mechanical strength of CMC was greatly enhanced by adding LDH nanoparticles. The elastic modulus of the CMC/LDH composite microneedles is comparable to that of engineering plastics, e.g. 2-4 GPa for nylon and 2.0-2.6 GPa for polycarbonate. This improvement has the capacity to increase the flexibility of drug and molecules formulations that can be incorporated into dissolving microneedle arrays. The addition of drugs and biomolecules, composed primarily of proteins and salts, may worsen the mechanical properties of the structural polymer in a concentration-dependent manner. The addition of reinforcing nanofillers may help to curb that effect such that the final microneedle array remains useful for animal and human applications.

The fabrication process described above was operated at room temperature (23° C.). Lowering the temperature to optimize the stability of the drug and molecules could be explored using this casting technique. The entire fabrication process required no heating, UV illumination or any other harsh conditions or treatments; therefore, this technique is suitable for incorporating drugs and delicate biomolecules into microneedles for subsequent transdermal delivery. The nanocomposite microneedles have excellent biocompatibility, similar to other widely studied and commonly considered as biocompatible nanoparticles such as gold nanoparticles, as confirmed by cell viability test. The enhanced mechanical properties of the CMC/LDH composite microneedles successfully pierced pig and human skin to deliver a FITC-labeled dextran payload. Importantly, the nanoparticle strengthened polymer microneedles retained the capacity to dissolve quickly, within only 1 minute. The composite microneedles delivered the FITC-labeled dextran payload up to around 64±9 μm below the human skin surface. The human epidermis layer contains high density of antigen-presenting cells (APCs) and its thickness, using human forearm dorsal epidermis as an example, is 61.3±11.0 μm. This means that most of the payload was delivered within the target layer.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

We claim:

1. A microneedle structure comprising a plurality of microneedles, wherein each of said microneedles is comprised of at least one dissolvable polymer and a nanomaterial, wherein said nanomaterial is well-dispersed throughout each of said microneedles, and wherein said nanomaterial comprises layered double hydroxide nanoparticles in a concentration between about 5 wt % and about 10 wt % relative to the mass of said polymer in the composite solution, and wherein said polymer comprises sodium carboxymethylcellulose.

2. The microneedle structure of claim 1, wherein said layered double hydroxide nanoparticles comprise at least one of magnesium, aluminum, iron, cobalt, zinc, calcium and manganese.

3. The microneedle structure of claim 1, wherein said polymer comprises negatively charged functional groups.

4. The microneedle structure of claim 1, wherein said microneedles further comprise at least one drug or biomolecule, and wherein said drug or biomolecule may optionally be associated with said nanomaterial to form a nanomedicine.

5. The microneedle structure of claim 1, wherein said microneedles are comprised of:
   layered double hydroxide nanoparticles comprising a positive charge on at least one surface;
   polymer comprising negatively charged functional groups; and
   a drug or biomolecule.

6. A method for producing the microneedle structure of claim 1, comprising:
   a. forming a composite solution comprising at least one dissolvable polymer and a nanomaterial comprising layered double hydroxide nanoparticles and optionally at least one drug or biomolecule, wherein said layered double hydroxide nanoparticles are well-dispersed throughout said composite solution;
   b. adding said composite solution to the surface of a microneedle structure mold;
   c. forcing said composite solution to the microneedle structure mold cavity;
   d. drying said composite solution to form a microneedle structure; and
   e. removing said microneedle structure from said microneedle structure mold;
   wherein said drug or biomolecule may optionally be associated with said nanomaterial to form a nanomedicine.

7. The method according to claim 6, wherein steps b, c, and d are repeated one or more times.

8. The method according to claim 6, wherein said nanomaterial comprises layered double hydroxide nanoparticles comprising a positive charge on at least one surface and wherein said polymer comprises negatively charged functional groups.

9. The method according to claim 6, wherein said method is performed at a temperature between about 4° C. and 37° C.

10. The method according to claim 6, wherein said drug or biomolecule is negatively charged.

11. The method according to claim 6, wherein the dissolution rate of said microneedle structure is within 25% of the dissolution rate of a microneedle structure comprising the at least one dissolvable polymer but free of the nanomaterial.

12. A method for delivering a drug or biomolecule transdermally or to the epithelia, or to the cytoplasm and/or nucleus of a cell within skin or epithelia, comprising applying the microneedle structure comprising a plurality of microneedles of claim 1, wherein each of said microneedles is comprised of
   a) at least one dissolvable polymer;
   b) a nanomaterial comprising layered double hydroxide nanoparticles; and
   c) said drug or biomolecule,
   wherein said layered double hydroxide nanoparticles are well-dispersed throughout each of said microneedles; to the skin or epithelia of a subject such that the microneedles of the microneedle structure penetrate the skin or epithelia and the drug or biomolecule is released upon the dissolution of said microneedles, and wherein said dissolution of said microneedles substantially occurs within five minutes of said penetration of the skin or epithelia;
   wherein said drug or biomolecule may optionally be associated with said nanomaterial to form a nanomedicine, and wherein said nanomedicine is released upon the dissolution of said microneedles.

13. The method according to claim 12, wherein said microneedles are comprised of layered double hydroxide nanoparticles comprising a positive charge on at least one surface and polymer comprising negatively charged functional groups.

14. The method according to claim 12, wherein the dissolution of said microneedles substantially occurs within one minute of said penetration of the skin or epithelia.

* * * * *